United States Patent [19]
Ono et al.

[11] Patent Number: 5,388,177
[45] Date of Patent: Feb. 7, 1995

[54] HEATING ELEMENT FOR DEODORIZATION

[75] Inventors: Yukiyoshi Ono, Hirakata; Kunio Kimura, Tsuzuki; Hidenobu Wakita, Yawata; Yasue Yamade, Hirakata, all of Japan

[73] Assignee: Matsushita Electric Industrial Co., Ltd., Osaka, Japan

[21] Appl. No.: 235,213

[22] Filed: Apr. 29, 1994

Related U.S. Application Data

[63] Continuation of Ser. No. 910,895, Jul. 10, 1992, abandoned.

[30] Foreign Application Priority Data

Jul. 16, 1991 [JP] Japan .................. 3-175092
Jul. 16, 1991 [JP] Japan .................. 3-175093

[51] Int. Cl.$^6$ .............................................. H05B 3/20
[52] U.S. Cl. .................................... 392/386; 338/262;
219/553; 55/DIG. 30; 422/174; 422/177; 60/300
[58] Field of Search ............... 392/386; 338/254, 262,
338/263, 275; 219/553, 548, 397–399; 60/300;
55/DIG. 30, 389, 387; 422/177, 180, 174

[56] References Cited

U.S. PATENT DOCUMENTS

| | | | |
|---|---|---|---|
| 2,658,742 | 11/1953 | Suter et al. | 55/DIG. 30 |
| 3,770,389 | 10/1973 | Kitzner et al. | 60/300 |
| 3,962,561 | 6/1976 | Maitenaz | 126/190 |
| 4,352,853 | 10/1982 | Uchikawa et al. | 428/304.4 |
| 4,780,277 | 10/1988 | Tanaka et al. | 422/172 |
| 5,078,981 | 1/1992 | Kagawa et al. | 423/239 |
| 5,094,074 | 3/1992 | Nishizawa et al. | 60/300 |
| 5,195,165 | 3/1993 | Ono et al. | 392/407 |

FOREIGN PATENT DOCUMENTS

| | | |
|---|---|---|
| 61008 | 9/1982 | European Pat. Off. . |
| 0170567 | 2/1986 | European Pat. Off. . |
| 0369576 | 5/1990 | European Pat. Off. . |
| 54-112981 | 9/1979 | Japan . |
| 55-41862 | 3/1980 | Japan . |
| 63-111185 | 5/1988 | Japan . |

*Primary Examiner*—Bruce A. Reynolds
*Assistant Examiner*—John A. Jeffery
*Attorney, Agent, or Firm*—Stevens, Davis, Miller & Mosher

[57] ABSTRACT

A heating element for deodorization contains a metallic substrate, an enamel layer formed on the surface of the metallic substrate, a catalyst layer comprising at least an active alumina, a platinum group metal and a zeolite and formed on the enamel layer, and an electric resistor; the electric resistor being insulated from the environment; and the metallic substrate, the enamel layer, the catalyst layer and the electric resistor being arranged so that heat generated when electric power is applied to the electric resistor is conducted to the catalyst layer through the enamel layer. It can remove unpleasant odor and harmful gases.

24 Claims, 1 Drawing Sheet

5,388,177

HEATING ELEMENT FOR DEODORIZATION

This application is a continuation of application Ser. No. 07/910,895, filed Jul. 10, 1992 (abandoned).

The present invention relates to heating elements for deodorization which are utilized in air conditioning, refrigerating, cooking or drying apparatuses.

The conventional heating elements include coiled metal wires such as nichrome wires and tantalum wires; metallic, quartz or ceramic tubes which have therein the above coiled metal wires; tubes obtained by coating the above tubes with cordierite, clay, glass or a material having high far-infrared-radiation properties such as nickel oxide or iron oxide; and ceramic heaters equipped with a ceramic-sintered body which has therein a resistor. Heaters, hot water supply devices and drying devices effect heating by the use of heat generated by such a heating element as mentioned above (thermal conduction), by the use of warm air generated by forcedly sending air from a fan to a heating element (thermal convection), or by the use of radiation of heat generated by providing a reflecting plate behind a heating element (thermal radiation).

The above-mentioned conventional heating elements have the following problems.

For example, when heating is effected by an electric stove, the heating element heats not only the air in a room, but also the tobacco smoke floating in the room or odorous substances in the room. In general, unpleasant odor is more offensive to the nose at higher temperatures. Moreover, the odorous substances once adsorbed in the room are again vaporized and float in the room. Since the conventional heating elements have no ability to remove the odorous substances, the use of an electric stove often brings about such phenomenon that the odor becomes more offensive as compared with the case where the electric stove is not used.

SUMMARY OF THE INVENTION

The present invention has been made in order to solve the problems of the conventional techniques. The object of the present invention is to provide a heating element which has a simple construction and can remove disagreeable odors or harmful gases.

According to the present invention, there are provided:

a heating element for deodorization which comprises a metallic substrate, an enamel layer formed on the surface of the metallic substrate, a catalyst layer comprising at least an active alumina, a platinum group metal and a zeolite and formed on the enamel layer, and an electric resistor; the electric resistor being insulated from the environment; and the metallic substrate, the enamel layer, the catalyst layer and the electric resistor being arranged so that heat generated when electric power is applied to the electric resistor is conducted to the catalyst layer through the enamel layer;

a heating element for deodorization which comprises a metallic substrate, an enamel layer formed on the surface of the metallic substrate, a catalyst layer comprising at least an active alumina, a platinum group metal and a zeolite and formed on the enamel layer, an electric resistor and an electric insulator provided for ensuring the electric insulation of the electric resistor; the electric resistor and the electric insulator being fixed on the metallic substrate in close contact with the substrate;

a heating element for deodorization which comprises a metallic tube having therein an electric resistor and electrically insulated from the electric resistor by an electric insulator, a metallic substrate having a high thermal conductivity and adhering to the metallic tube, an enamel layer formed on the surface of the metallic substrate, and a catalyst layer comprising at least an active alumina, a platinum group metal and a zeolite and formed on the enamel layer;

a heating element for deodorization which comprises a metallic substrate, an enamel layer formed on the surface of the metallic substrate, an electric resistor embedded in the enamel layer, and a catalyst layer comprising at least an active alumina, a platinum group metal and a zeolite and formed on the enamel layer; and a heating element for deodorization which comprises a metallic substrate, an enamel layer, a catalyst layer comprising at least an active alumina, a platinum group metal and a zeolite, and an electric resistor; the catalyst layer being set apart from the metallic substrate and the electric resistor by the enamel layer.

DESCRIPTION OF THE INVENTION

The steps of deodorization according to the present invention are as follows: The odorous substances in a room are adsorbed by the zeolite and active alumina contained in the catalyst layer. Then, the electric resistor is supplied with electric current to generate heat before the zeolite and the active alumina have adsorbed the odorous substances to their adsorptive limitations. The catalyst layer is effectively heated by heat transferred from the electric resistor. As a result, the catalyst layer is heated up to the activation temperature of the catalysts in a short time. The activated catalysts then oxidize and decompose the adsorbed odorous substances. Additionally, the heating element also heats the air in the vicinity thereof and causes air streams around the heating element due to convection. When the air streams contact with the catalyst layer heated to a temperature higher than the activation temperature by the heating element, the odorous substances or harmful substances in the air streams are adsorbed to the catalyst layer, oxidized and purified by the catalytic action thereof and released from the catalyst layer.

The action of the heating element is explained hereabove with reference to natural convection which occurs near the heating element, but more conspicuous effect is obtained when air is forcedly fed to the heating element by a fan and the present invention also includes the use of a fan in its scope.

Figure 1:
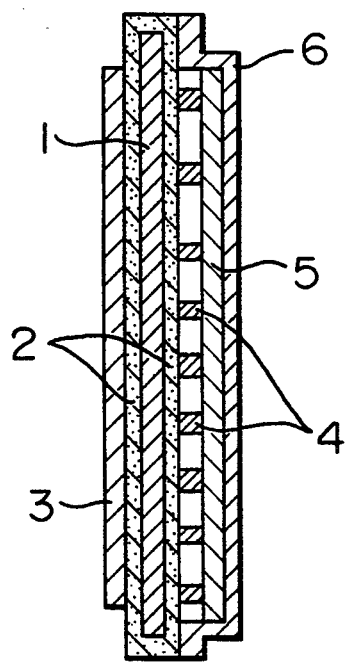
FIG. 1 shows one example of the heating element according to the present invention.

One example of the heating element of the present invention is shown in FIG. 1.

In FIG. 1, 1 indicates a metallic substrate, 2 indicates an enamel layer, 3 indicates a catalyst layer provided on the surface of the enamel layer, 4 indicates an electric resistor which adheres to the enamel layer, 5 indicates mica as an electric insulator and 6 indicates a metal fixture, and the electric resistor 4 is electrically insulated from the surroundings by the enamel layer 2 and the electric insulator 5.

As the metallic substrate, there may be used aluminum, steels for porcelain enamel, aluminized steels, stainless steels and the like. These may be used in various forms depending on the purposes, such as in platy, tubular, curved and honeycomb forms.

As the materials for the enamel layer, there may be used silicate glass, borosilicate glass, crystallized glass and the like.

Specific examples of the electric resistors are metallic resistors such as stainless steel, nichrome, SiC and tungsten and PTC ceramic resistors.

Specific examples of the electric insulators are mica, ceramics, glasses and porcelain.

Furthermore, a sheathed heater in which an electric resistor and an electric insulator are combined may also be used in the present invention.

The steps of deodorization according to the present invention are as follows: The odorous substances in a room are usually adsorbed by the zeolite and active alumina in the catalyst layer 3. Before the zeolite and the active alumina have adsorbed the odorous substances to their adsorptive limitations, the electric resistor 4 is applied with electric current to generate heat. The heat thus generated is conducted to the metallic substrate 1 through the enamel layer 2. The heat conducted to the metallic substrate 1 rapidly diffuses thereinto, whereby the metallic substrate 1 is uniformly heated. Moreover, the portion of the enamel layer 2 between the catalyst layer 3 and the metallic substrate 1 is also relatively uniformly heated. As a result, the catalyst layer 3 formed on the surface of the enamel layer 2 is also uniformly heated, and the catalyst in the catalyst layer 3 is activated in a short time. The odorous substances adsorbed in the catalyst layer 3 are rapidly oxidized and decomposed by the activated catalysts. In addition, since the heating element also heats the air near the heating element, air streams are produced near the heating element due to convection. When the air streams contact with or diffuse into the catalyst layer 3 which has been heated up to the activation temperature by the heat from the electric resistor 4, unpleasant odors or harmful components such as carbon monoxide (hereinafter referred to as CO) and ammonia contained in the air near the heating element are oxidized and purified by the catalytic action.

The zeolite-and alumina heated by the above mentioned heating means are restored in their adsorption capacity due to the release of the adsorbed odorous substances by oxidative decomposition. Thus, they can again adsorb odorous substances after the heating by the above heating means has been stopped. In this way, by alternatively repeating the step of the adsorption of odorous substances by the zeolite and alumina in non-heated state and the step of regeneration of the zeolite and alumina and the oxidative decomposition of the odorous substances by platinum group metals in heated state, unpleasant odors can be continuously removed over a long period of time without causing so much increase in the temperature around the catalysts.

Thus, the heating element of the present invention adsorbs and thermally decomposes the unpleasant odors, tobacco smokes or harmful gases such as CO floating in the environment where a heating element is placed thereby to provide a pleasant environment.

In the present invention, the enamel layer is formed between the metallic substrate and the catalyst layer. In the above-mentioned mechanism, the enamel layer is not always necessary; however, if the catalyst layer and the metallic substrate directly contact with each other, corrosion of the metallic substrate proceeds due to the action of local cell at the interface between the catalyst layer and the metal. On the other hand, when the enamel layer is provided so that the catalyst layer is set apart from the metallic substrate and the electric resistor according to the present invention, the corrosion can be inhibited and besides, the adhesion of the catalyst layer can be improved.

The heating element of the present invention is equipped with a catalyst layer containing at least an active alumina, a zeolite and a platinum group metal. The combined use of the active alumina, zeolite and platinum group metal provides a synergistic effect and unexpectedly improves the adsorption capacity for acidic odorous substances as compared with the use of them each alone.

As the platinum group metals used in the present invention, Pt and Pd are preferred. The combined use of them is more preferred. This is because Pt and Pd are higher than Rh and Ir in oxidative decomposition power, and the combined use of Pt and Pd further improves the oxidative decomposition power. Ru tends to be volatilized when used at elevated temperatures and be converted to harmful substances. It is preferable to support the platinum group metal on the alumina. This is because supporting a platinum group metal on alumina possibly improves the activity for oxidative decomposition of the catalyst. The platinum group metal can be supported on the alumina by various methods, and the methods are not critical for the present invention. For example, it can be effected by dipping alumina in an aqueous solution of a salt of a platinum group metal, drying the dipped alumina and calcining the dried alumina.

The content of the platinum group metal for obtaining a synergistic effect that improves the adsorption capacity for acidic odorous substances is preferably between 0.1% by weight and 8% by weight in the catalyst layer. When the content is less than 0.1% by weight, the synergistic effect sometimes cannot be obtained. When it is more than 8% by weight, the synergistic effect is sometimes reduced.

The catalyst layer of the present invention preferably contains cerium oxide. The incorporation of cerium oxide into the catalyst layer further improves the oxidative decomposition activity of the catalysts for hydrocarbon compounds.

The content of cerium oxide is preferably between 2% by weight and 15% by weight in the catalyst layer. When the content of cerium oxide exceeds 15% by weight, the oxidative decomposition activity of the catalysts tends to be reduced. When it is less than 2% by weight, the advantage obtained by incorporating cerium oxide tends to be small.

The catalyst layer of the present invention preferably contains titanium oxide. The incorporation of titanium oxide into the catalyst layer further improves the oxidation activity of the catalysts for nitrogen compounds such as ammonia.

The content of titanium oxide is preferably between 3% by weight and 15% by weight in the catalyst layer.

When the content exceeds 15% by weight, the adhesion of the catalyst layer tends to be deteriorated. When it is less than 3% by weight, the advantage obtained by incorporating titanium oxide tends to be small.

The specific surface area of the catalyst layer of the present invention is preferably 10 m$^2$/g or more. This is because as the specific surface area of the catalyst layer increases, the proportion of the far infrared radiation to the near infrared radiation increases. And a sufficiently high proportion of far infrared radiation can usually be obtained when the specific surface area is 10 m$^2$/g or more.

The catalyst layer can be formed by various methods such as spray coating, dip coating, electrostatic coating, roll coating and screen printing; however, the methods are not critical in the present invention.

In the example of FIG. 1, the electric resistor 4 is electrically insulated by the enamel layer 2 and the electric insulator 5. However, it is also possible to employ a construction in which the electric resistor is sandwiched between a pair of electric insulators, or alternatively, a construction in which the electric resistor is built in an electric insulator (for example, construction of sheathed heater) for ensuring the electric insulation of metallic substrate from the electric resistor.

Furthermore, in FIG. 1, the catalyst layer is formed on the whole surface of one side of the enamel layer; however, it may not necessarily be formed on the whole surface. It may be formed on a part of the surface of the enamel layer, for example, so as to make an optional pattern. Besides, the surface of the enamel layer may be roughened for further improving the adhesion of the catalyst layer to the enamel layer.

Figure 2:
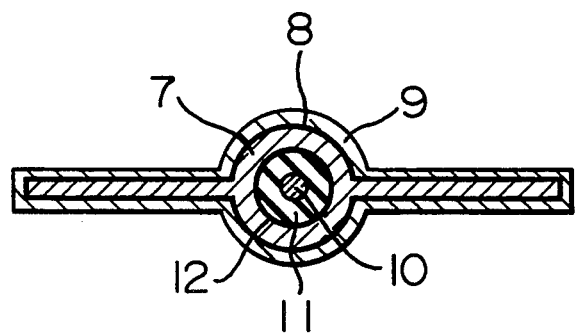
FIG. 2 shows another example of the heating element according to the present invention.

FIG. 2 shows another example of the heating element of the present invention which uses a sheathed heater. In FIG. 2, 10 indicates an electric resistor; 11 indicates an electric insulator; 12 indicates a stainless steel tube having therein 10 and 11; and 10, 11 and 12 form a sheathed heater. Aluminum fin 7 having a high thermal conductivity is provided in close contact with the above sheathed heater. Enamel layer 8 is formed on the surface of the alumina fin 7 and catalyst layer 9 is formed on the surface of the enamel layer 8.

According to this example, the odorous substances in a room are usually adsorbed by the zeolite and active alumina in the catalyst layer 9 and deodorized. Before the zeolite and the active alumina have adsorbed the odorous substances to their adsorptive limitations, the electric resistor 10 is applied with electric current to generate heat. The heat thus generated is conducted to the aluminum fin 7 which closely surrounds the electric resistor 10. The heat conducted to the aluminum fin 7 having a high thermal conductivity rapidly diffuses thereinto, whereby the aluminum fin 7 is uniformly heated. Moreover, the catalyst layer 9 formed on the surface of enamel layer 8 around the aluminum fin 7 is also uniformly heated, and the catalyst in the catalyst layer 9 is activated in a short time. The odorous substances adsorbed in the catalyst layer 9 are rapidly oxidized and decomposed by the activated catalysts. In addition, since the heating element also heats the air near the heating element, air streams are produced near the heating element due to convection. When the air streams contact with or diffuse into the catalyst layer 9 which had been heated up to the activation temperature, odors or harmful gases such as CO and ammonia contained in the air near the heating element are oxidized and purified. The zeolite and aluminum heated by the above mentioned heating means are restored in their adsorption capacity due to the release of the adsorbed odorous substances after the heating had been stopped. In this way, by alternatively repeating the step of the adsorption of odorous substances by the zeolite and alumina in non-heated state and the step of regeneration of the zeolite and alumina and the catalytic decomposition of the odorous substances in heated state, unpleasant odors can be continuously removed over a long period of time without causing so much increase in the temperature around the catalysts.

By providing a metallic substrate having a high thermal conductivity around the tubular heater such as sheathed heater in close contact with each other and forming a catalyst layer on the surface of the metallic substrate as shown in FIG. 2, the heat generated from the heater can be more efficiently used for heating of the catalyst layer than in the case of the heating element having the construction as shown in FIG. 1. Furthermore, the substrate area for formation of the catalyst layer which is one of the governing factors which determine adsorption capacity for odorous substances is enlarged by using a metallic substrate provided with a fan and performance of the heating element can be improved.

Specific examples of the metallic substrates of high thermal conductivity used in the present invention are aluminum, aluminum alloys, silver, copper and copper alloys. Preferred are those having a thermal conductivity at 100° C. of 0.3 cal.cm$^{-1}$.sec$^{-1}$.deg$^{-1}$ or more.

In the construction shown in FIG. 2, the enamel layer 8 and the catalyst layer 9 are formed on the surface of the aluminum fin 7. However, the enamel layer 8 and the catalyst layer 9 may be formed directly on the surface of the stainless steel tube of the sheathed heater.

The catalyst layer of the present invention preferably contains silica. The incorporation of silica into the catalyst layer can strengthen the adhesion of the catalyst layer to the substrate.

The content of silica is preferably between 6% by weight and 40% by weight. When the content exceeds 40% by weight, cracks are liable to occur in the catalyst layer, and the adhesion tends to be deteriorated. When it is less than 6% by weight, the improvement in adhesion by the incorporation of silica tends to be small.

The catalyst layer of the present invention contains at least one zeolite. The incorporation of zeolite into the catalyst layer enables the adsorption of odorous substances in non-heated state. Unpleasant odors can be continuously removed over a long period of time without causing much increase of temperature around the heating element by alternately repeating the step of the above-mentioned adsorption under the non-heated state and the step of the regeneration of zeolite by heating and the catalytic decomposition of odorous substances under the heated state. Various kinds of zeolites can be used in the present invention. Among them, copper ion-exchanging zeolites have the highest odor adsorption capacity and are preferred.

EXAMPLE 1

Heating elements as shown in FIG. 1 were prepared by forming 0.2 g of a catalyst layer 3 which contained 0.1% by weight of platinum, 20% by weight of a copper ion-exchanged zeolite, various amounts of from 0 to 60% by weight of silica (in terms of silica) and the remainder of alumina on the surface of a SUS 304 sheet 1 of 1 mm in thickness, 100 mm in length and 100 mm in width, which sheet had a borosilicate glass enamel layer 2 of 50 μ in thickness. These heating elements were subjected to a thermal shock test to examine the adhesion of the catalyst layer 3. The thermal shock test was conducted in the following manner. The electric resistor 4 in FIG. 1 was supplied with electric current to set the temperature of the catalyst layer 3 at every 25° C. The heating element was kept at that temperature for 10 minutes. Thereafter, the heating element was introduced into water at room temperature and whether the catalyst layer 3 peeled or not was examined. The maximum temperature at which the catalyst layer 3 did not peel was taken as the thermal shock resistant temperature. The results are shown in Table 1.

As can be seen from Table 1, the highest adhesion (thermal shock resistance) was obtained with the silica content being 10–40% by weight.

TABLE 1

| Content of silica (wt %) | Thermal shock resistant temperature (°C.) |
| --- | --- |
| 0 | 400 |
| 3 | 450 |
| 4 | 475 |
| 6 | 575 |
| 8 | 650 |
| 9 | 675 |
| 10 | 700 |
| 35 | 700 |
| 38 | 700 |
| 39 | 700 |
| 40 | 700 |
| 41 | 650 |
| 42 | 625 |
| 45 | 550 |
| 50 | 525 |

EXAMPLE 2

Heating elements were prepared in the same manner as in Example 1, except that in place of the copper ion-exchanged zeolite, various zeolites as shown in Table 2 were used in the same amount as in Example 1 in catalyst layer 3. The adsorption capacity of these heating elements for odorous substances at the time when the electric resistor was not applied with electric current at room temperature was tested using methyl mercaptan, a representative odorous substance. The test was conducted in the following manner. The heating element was put in a closed box having a volume of 0.1 m³. The inner surface of the box was coated with fluorocarbon resin. In the box had been charged methyl mercaptan of 10 ppm in concentration diluted with air. The methyl mercaptan in the box was adsorbed in the heating element. The amount of residual methyl mercaptan was measured after elapse of 30 minutes just after the heating element was put in the box. This was taken as the adsorption capacity for methyl mercaptan. The air in the box was stirred by a fan during the test. The results are shown in Table 2.

As can be seen from Table 2, it was the copper ion-exchanged zeolite that showed the highest adsorption capacity for the odorous substance. Thus, this type of zeolite is preferred.

TABLE 2

| Ion species exchanging the zeolites | Residual methyl mercaptan (%) |
| --- | --- |
| Cu | 5 |

TABLE 2-continued

| Ion species exchanging the zeolites | Residual methyl mercaptan (%) |
| --- | --- |
| Na | 25 |
| Ca | 32 |
| Mg | 15 |
| Mn | 27 |
| Zn | 20 |
| Mordenite | 28 |

EXAMPLE 3

In the same manner and in the same construction as in Example 1, a heating element 1 of the present invention was prepared by forming 0.2 g of catalyst layer 3 containing 0.1% by weight of platinum, 20% by weight of a copper ion-exchanged zeolite, 20% by weight of silica in terms of silica and the remainder of alumina on the surface of SUS 304 sheet 1 of 1 mm in thickness, 100 mm in length and 100 mm in width, which sheet had an enamel layer 2. A comparative heating element 1 was prepared in the same manner as above, except that a SUS 304 sheet 1 having no enamel layer 2 was used. Another comparative heating element 2 was prepared as above using a SUS 304 sheet 1 having no enamel layer 2 but not forming a catalyst layer. The resulting heating element 1 and comparative heating elements 1 and 2 were placed in a thermohydrostat of 30° C.—RH 90% and the number of days before the SUS 304 sheet began to form rust were measured. The results are shown in Table 3.

Although the metallic substrate SUS 304 sheet formed rust with difficulty when it was used alone (see comparative heating element 2), the sheet formed rust in 7 days when it is used with a catalyst layer thereon (see comparative heating element 2). In contrast, the formation of rust could be prevented by providing an enamel layer as an insulating layer between the metallic substrate and the catalyst layer according to the present invention.

TABLE 3

| | Number of days before sheet began to form rust |
| --- | --- |
| Heating element 1 | More than 100 days |
| Comparative heating element 1 | 7 days |
| Comparative heating element 2 | More than 100 days |

EXAMPLE 4

400 grams of γ-alumina, 100 g of aluminum hydroxide as an inorganic binder, 500 g of a copper ion-exchanged zeolite, 1,500 g of water, 30 g (in terms of Pt) of chloroplatinic acid, 15 g (in terms of Pd) of palladium chloride and a suitable amount of hydrochloric acid were thoroughly mixed by a ball mill to prepare slurry A. The slurry A was spray coated on the surface of a SUS 304 sheet 1 of 1 mm in thickness, 100 mm in length and 100 mm in width, which sheet had thereon a borosilicate glass enamel layer 2 of 50μ in thickness. The slurry-coated sheet was then dried at 100° C. for 2 hours and fired at 500° C. for 1 hour to thermally decompose the aluminum hydroxide and the salts of platinum group metals. As a result, a catalyst layer containing γ-alumina and platinum group metals as catalysts was formed on the SUS 304 sheet. A heating element 2 as shown in FIG. 1 was prepared using the thus obtained metallic substrate having a catalyst layer thereon. The amount of the catalyst layer was 0.2 g.

Separately, 445 g of γ-alumina on which the same amounts of platinum and palladium as in the slurry A were previously supported using chloroplatinic acid and palladium chloride, 100 g of aluminum hydroxide as an inorganic binder, 500 g of a copper ion-exchanged zeolite and 1,500 g of water were thoroughly mixed by a ball mill to prepare slurry A'. In the same manner as in preparation of the heating element 2, 0.2 g of a catalyst layer was formed on a SUS 304 sheet using the slurry A'. Using the resulting metallic substrate, heating element 3 having the same construction as shown in FIG. 1 was prepared.

These heating elements 2 and 3 were subjected to a test on cleansing of methyl mercaptan by oxidation in order to compare the catalyst activities thereof. The test was conducted in the following manner. The heating element was placed in a cubic fluorocarbon resin container of 0.1 m³ and was heated so that the temperature of the outer surface of the center of the heating element reached 450° C. At this temperature, methyl mercaptan was injected into the container at a concentration of 10 ppm. The change of the methyl mercaptan concentration with the lapse of time was detected by gas chromatograph. The results are shown in Table 4.

As can be seen from Table 4, the heat element had a higher activity than the heating element 2. Thus, the capacity of the heating element for oxidative decomposition of odorous substances could be improved by supporting platinum group metals on an active alumina.

TABLE 4

| Elapsed time (min) | Percentage of residual mercaptan when heating element 2 was used (%) | Percentage of residual mercaptan when heating element 3 was used (%) |
| --- | --- | --- |
| 2 | 92 | 90 |
| 5 | 60 | 45 |
| 10 | 34 | 14 |
| 30 | 7 | 4 |

EXAMPLE 5

Comparative slurry 1 was prepared by omitting the salts of platinum group metals from the slurry A of Example 4. Comparative slurry 2 was prepared by omitting the salts of platinum group metals and replacing the γ-alumina with the copper ion-exchanged type zeolite in the slurry A, namely, using 900 g of the copper ion-exchanged type zeolite while omitting the γ-alumina. Comparative slurry 3 was prepared by omitting the salts of platinum group metals and replacing the copper ion-exchanged type zeolite with the γ-alumina in the slurry A, namely, using 900 g of the γ-alumina while omitting the copper ion-exchanged type zeolite. Using these comparative slurries 1, 2 and 3, comparative heating elements 3, 4 and 5 having 1.0 g of the respective catalyst layers were prepared in the same manner as in preparation of the heating element 2.

The resulting comparative heating elements 3, 4 and 5 were subjected to an acetic acid adsorbing test. These heating elements were compared with the heating element 2 according to the present invention in percentage of residual acetic acid after elapse of 60 minutes from the starting of the test. The test was conducted in the following manner. The heating element was placed in a cubic fluorocarbon resin container of 0.25 m³. Acetic acid was injected into the container at a concentration of 40 ppm without heating the heating element. The change of the acetic acid concentration with the lapse of time was detected by gas chromatograph.

The results are shown in Table 5. As can be seen from Table 5, the heating element 2 according to the present invention was superior to the comparative heating elements 3, 4 and 5 in adsorption capacity of acetic acid, an acidic odorous substance. Thus, it was found that the combined use of an active alumina, a zeolite and platinum group metals showed a synergistically improved adsorption capacity for acidic odorous substances as compared with the use of an active alumina or a zeolite each alone. Also it was found that the combined use of an active alumina, a zeolite and platinum group metals showed a higher adsorption capacity for acidic odorous substances than did the use of an active alumina and a zeolite without platinum group metals.

TABLE 5

| | Percentage of residual acetic acid after elapse of 60 min |
| --- | --- |
| Heating element 2 | 52 |
| Comparative heating element 3 | 60 |
| Comparative heating element 4 | 78 |
| Comparative heating element 5 | 85 |

Additionally, in the same manner as in preparation of slurry A of Example 4, slurries containing 0–10% by weight of platinum in its solid content were prepared by using chloroplatinic acid as a sole source of platinum group metals. By using the thus prepared slurries, heating elements having the construction as shown in FIG. 1 and having 1.0 g of the catalyst layer were prepared.

The heating elements were subjected to the acetic acid adsorbing test in the same manner as conducted above. They were compared in percentage of residual acetic acid after elapse of 60 minutes from the starting of the test.

Table 6 shows the results. It demonstrates that when the content of the platinum group metal is less than 0.1% by weight, sufficient synergistic effect such as that mentioned above cannot be obtained; and when the content is more than 8% by weight, in turn, the synergistic effect is reduced.

Therefore, in order to obtain such a synergistic effect that improves the adsorption capacity for acidic odorous substances, it is preferable to incorporate the platinum group metal in an amount of 0.1–8% by weight into the catalyst layer.

TABLE 6

| Content of Pt (wt %) | Percentage of residual active acid after elapse of 60 minutes (%) |
| --- | --- |
| 0 | 60 |
| 0.08 | 55 |
| 0.09 | 54 |
| 0.1 | 53 |
| 0.2 | 53 |
| 0.5 | 53 |
| 1.0 | 53 |
| 2.0 | 53 |
| 5.0 | 53 |
| 7.0 | 53 |
| 8.0 | 53 |
| 9.0 | 55 |

TABLE 6-continued

| Content of Pt (wt %) | Percentage of residual active acid after elapse of 60 minutes (%) |
|---|---|
| 10.0 | 58 |

EXAMPLE 6

Figure 3:
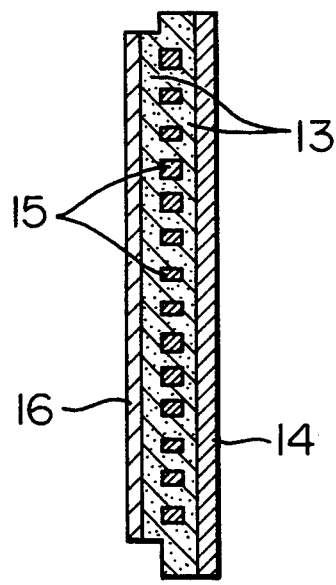
FIG. 3 shows still another example of the heating element according to the present invention.

In FIG. 3, 13 indicates an enamel layer, 14 indicates a metallic substrate, 15 indicates an electric resistor embedded in the enamel layer and 16 indicates a catalyst layer formed on the surface of the enamel layer.

When electric resistor 15 is applied with electric current, the electric resistor 15 generates heat, which is transferred, due to thermal transfer, to the catalyst layer 16 formed on the enamel layer 13 through the enamel layer, whereby the catalyst layer 16 is heated. Since the electric resistor 15 and the catalyst layer 16 are close to each other, the heating of the catalyst layer 16 is performed efficiently and rapidly, and the platinum group metal in the catalyst layer 16 is heated, up to the activation temperature in a short time. Since the enamel layer 13 is formed on the surface of the metallic substrate 14, the heat of the electric resistor 15 is also transferred to the metallic substrate 14 through the enamel layer 13. The heat transferred to the metallic substrate 14 rapidly diffuses thereinto and thus the metallic substrate 14 is uniformly heated and furthermore, the enamel layer 13 formed on the surface of the metallic substrate is also relatively uniformly heated. As a result, the portion of the catalyst layer 16 formed on the enamel layer 13 which is not present just above the electric resistor 15 is also rapidly heated like the catalyst layer 16 just above the electric resistor 15 and is activated. In addition, since the heating element also heats the air in the vicinity of the heating element, air streams are produced near the heating element due to convection. When the air streams contact with or diffuse into the catalyst layer 16 heated up to the activation temperature by the heat from the electric resistor 15, unpleasant odors or harmful components such as CO and ammonia contained in the air near the heating element are oxidized and purified by the catalytic action.

In the case of the heating element shown in FIG. 3, the distance between the electric resistor and the catalyst layer can be shortened as compared with the cases of the heating elements shown in FIGS. 1 and 2, and as a result, the catalyst layer can be heated and activated in a shorter time. Furthermore, the heating element can be made such more compact.

In this example, the electric resistor is embedded in the enamel layer. However, it may be possible to coat the electric resistor with a glass and adhere the glass-coated electric resistor to the metallic substrate with an adhesive such as another glass. Or alternatively, the electric resistor may be mechanically adhered to the metallic substrate by an adhering jig.

EXAMPLE 7

Heating elements having 0.2 g of catalyst layer were prepared in the same manner as in preparation of the heating element 2, in Example 4 while changing the content of the active alumina ($\gamma$-alumina) in the range of 10–85% by weight based on the total solid content in the catalyst layer and while reducing the amount of the copper ion-exchanging zeolite corresponding to the increment of the active alumina. These heating elements were subjected to the same thermal shock test as in Example 1 so as to examine the adhesion of the catalyst layer. The thermal shock resistance was conducted in the same manner as in Example 1.

The adsorption capacity of these heating elements for odorous substances when the nichrome wire was not yet applied with electric current was tested using methyl mercaptan, a representative odorous substance. The test was conducted in the same manner as in Example 2. The results are shown in Table 7.

As can be seen from Table 7, when the content of the active alumina is less than 20% by weight, the thermal shock resistant temperature is reduced, and when it is more than 80% by weight, the concentration of the residual mercaptan is high, and the adsorption capacity for odorous substances is reduced. Thus, when the content of the active alumina is in the range of 20–80% by weight, the highest adhesion (thermal shock resistance) and adsorption capacity for odorous substance and obtained, and this range is preferred.

TABLE 7

| Content of active alumina (wt %) | Thermal shock resistant temperature (°C.) | Percentage of residual methyl mercaptan (%) |
|---|---|---|
| 10 | 150 | 5 |
| 15 | 275 | 5 |
| 18 | 350 | 5 |
| 20 | 400 | 5 |
| 25 | 400 | 5 |
| 30 | 400 | 5 |
| 40 | 400 | 5 |
| 60 | 400 | 5 |
| 75 | 400 | 5 |
| 80 | 400 | 5 |
| 82 | 400 | 9 |
| 85 | 400 | 17 |

EXAMPLE 8

Heating elements were prepared in the same manner as in preparation of heating element 2 in Example 4 except that in place of the borosilicate glass enamel layer 2, various films as shown in Table 8 were formed as protective film layers on the surface of SUS 304 sheet of 1 mm in thickness, 100 mm in length and 100 mm in width, and the same catalyst layer as in Example 4 was formed thereon. These heating elements were subjected to the same thermal shock test as in Example 1 to examine the adhesion of the catalyst layer, and besides, they were subjected to the same rust proofing test as in Example 3. The results are shown in Table 8.

As can be seen from Table 8, the borosilicate glass gave the highest rust proofness and film adhesion (thermal shock resistance) as a protective film material.

TABLE 8

| Protective film materials | Number of days before beginning of formation of rust | Thermal shock resistant temperature (°C.) |
|---|---|---|
| Borosilicate glass | More than 100 days | 400° C. |
| Polysilicate | More than 100 days | 275° C. |
| Oxide film of metallic substrate | 16 days | 325° C. |
| Water-glass + $MnO_2$ | More than 100 days | 350° C. |

As described above, according to the present invention, unpleasant odors or harmful gases such as tobacco smoke in the atmosphere in which the heating element is placed are removed by catalytic action. Thus, a comfortable heated environment can be provided by the use of the heating elements.

What is claimed is:

1. A heating element for deodorization comprising: a metallic substrate; an enamel layer formed on a surface of the metallic substrate; a catalyst layer formed on the enamel layer and comprising at least an active alumina, a platinum group metal and a zeolite having only one exchanged ion, said one exchanged ion being selected from the group consisting of Cu and Mg; and an electric resistor which is insulated from an environment surrounding the heating element; and the metallic substrate, the enamel layer, the catalyst layer and the electric resistor being disposed relative to one another so that heat generated when electric power is applied to the electric resistor is conducted to the catalyst layer through the enamel layer.

2. The heating element for deodorization of claim 1, wherein the electric resistor comprises an electric insulator for ensuring electric insulation of the electric resistor; the electric resistor including the electric insulator being fixed on the metallic substrate in close contact with the metallic substrate.

3. The heating element for deodorization of claim 2, wherein the catalyst layer further comprises silica.

4. The heating element for deodorization of claim 2, wherein the zeolite is a copper ion-exchanged zeolite.

5. The heating element for deodorization according to claim 2, wherein the catalyst layer further comprises cerium oxide.

6. The heating element for deodorization of claim 2, wherein the catalyst layer further comprises titanium oxide.

7. The heating element for deodorization of claim 2, wherein the content of the platinum group metal in the catalyst layer is between 0.1% by weight and 8% by weight.

8. The heating element for deodorization of claim 2, wherein the catalyst layer has a specific surface area of 10 $m^2/g$ or more.

9. The heating element for deodorization of claim 1, further comprising a metallic tube in which the electric resistor is disposed and an electric insulator for insulating the electric resistor from the metallic tube, and wherein the metallic substrate has a high thermal conductivity and is adhered to the metallic tube.

10. The heating element for deodorization of claim 9, wherein the catalyst layer further comprises silica.

11. The heating element for deodorization of claim 9, wherein the zeolite is a copper ion-exchanged zeolite.

12. The heating element for deodorization of claim 9, wherein the catalyst layer further comprises cerium oxide.

13. The heating element for deodorization of claim 9, wherein the catalyst layer further comprises titanium oxide.

14. The heating element for deodorization of claim 9, wherein the content of the platinum group metal in the catalyst layer is between 0.1% by weight and 8% by weight.

15. The heating element for deodorization of claim 9, wherein the catalyst layer has a specific surface area of 10 $m^2/g$ or more.

16. The heating element for deodorization of claim 1, wherein the electric resistor is embedded in the enamel layer.

17. The heating element for deodorization of claim 16, wherein the catalyst layer further comprises silica.

18. The heating element for deodorization of claim 16, wherein the zeolite is a copper ion-exchanged zeolite.

19. The heating element for deodorization of claim 16, wherein the catalyst layer further comprises cerium oxide.

20. The heating element for deodorization of claim 16, wherein the catalyst layer further comprises titanium oxide.

21. The heating element for deodorization of claim 16, wherein the content of the platinum group metal in the catalyst layer is between 0.1% by weight and 8% by weight.

22. The heating element for deodorization of claim 16, wherein the catalyst layer has a specific surface area of 10 $m^2/g$ or more.

23. A heating element for deodorization comprising: a metallic substrate; an enamel layer on the metallic substrate; a catalyst layer comprising at least an active alumina, a platinum group metal and a zeolite having only one exchanged ion, said one exchanged ion being selected from the group consisting of Cu and Mg; and an electric resistor; the catalyst layer being separated from the metallic substrate and the electric resistor by the enamel layer.

24. A method of removing an odorous substance from a gas, said method comprising:
   providing a catalyst comprising an active alumina, a platinum group metal and a zeolite having one exchanged ion, said one exchanged ion being selected from the group consisting of Cu and Mg;
   providing means for heating said catalyst;
   exposing said gas to said catalyst while said means for heating does not operate, said odorous substance being adsorbed on said catalyst; and
   heating said catalyst with said means for heating to cause catalysis of said odorous substance adsorbed on said catalyst.

* * * * *